United States Patent [19]
Morpeth

[11] Patent Number: 5,464,851
[45] Date of Patent: Nov. 7, 1995

[54] BIOCIDE COMPOSITION AND USE

[75] Inventor: Fraser F. Morpeth, Newark, Del.

[73] Assignee: Zeneca Limited, London, England

[21] Appl. No.: 281,975

[22] Filed: Jul. 29, 1994

Related U.S. Application Data

[62] Division of Ser. No. 5,422, Jan. 19, 1993, Pat. No. 5,364,874, which is a continuation of Ser. No. 689,623, Apr. 23, 1991, abandoned.

[30] Foreign Application Priority Data

Apr. 27, 1990 [GB] United Kingdom ............ 9009529

[51] Int. Cl.$^6$ .......... A01N 43/80; A01N 37/34; C14C 9/00; C10M 133/24; C10M 133/38; C09D 5/14; B27K 3/00; C07C 7/20
[52] U.S. Cl. .......... 514/373; 514/372; 514/526; 422/28; 422/35; 504/150; 504/156; 71/DIG. 1; 252/8.57; 252/9; 252/45; 252/49; 252/49.3; 252/49.5; 252/50; 106/18.32; 106/18.33; 106/20 R; 106/125; 44/300; 585/2; 585/4; 8/636; 208/14; 208/18; 208/19; 162/161; 523/122; 428/540; 428/541
[58] Field of Search .......... 514/373, 372, 514/526; 422/28, 35; 504/150, 156; 71/DIG. 1; 252/8.57, 9, 45, 49, 49.3, 49.5, 50; 106/18.32, 18.33, 20 R, 125; 44/300; 585/2, 4; 8/636; 208/14, 18, 19; 162/161; 523/122; 428/540, 541

[56] References Cited

U.S. PATENT DOCUMENTS

| | | | |
|---|---|---|---|
| 3,833,731 | 9/1974 | Grier et al. | 514/526 |
| 4,708,959 | 11/1987 | Shroot et al. | 514/373 |
| 5,034,405 | 7/1991 | Jakubowski | 514/526 |
| 5,373,016 | 12/1994 | Brown et al. | 514/372 |

FOREIGN PATENT DOCUMENTS

| | | |
|---|---|---|
| 0098410 | 1/1984 | European Pat. Off. |
| 0196452 | 10/1986 | European Pat. Off. |
| 2087388 | 5/1982 | United Kingdom |
| 2208474 | 4/1989 | United Kingdom |

OTHER PUBLICATIONS

Patent Abstracts of Japan, vol. 9, No. 134 (JP 60 19 704) (Jan. 31, 1985).

Hodges et al, "Detection and Measurement of Combined Biocide Action", in Denyer and Hugo, Mechanisms of Action of Chemical Biocides (1991) pp. 297–310.

Primary Examiner—Allen J. Robinson
Assistant Examiner—John Pak
Attorney, Agent, or Firm—Cushman Darby & Cushman

[57] ABSTRACT

A composition which contains a 2-halo-2-halomethyl glutaronitrile and a 4,5-polymethylene-4-isothiazolin-3-one. The compositions exhibit anti-microbial activity and certain combinations of isothiazolinones together with the glutaronitrile are surprisingly effective against both bacteria and fungi.

13 Claims, No Drawings

BIOCIDE COMPOSITION AND USE

This is a division of application Ser. No. 08/005,422, filed Jan. 19, 1993, which is now U.S. Pat. No. 5,364,874, which is a continuation of Ser. No. 07/689,623, filed Apr. 23, 1991, now abandoned.

The present invention relates to compositions which are useful as industrial biocides.

Industrial biocides are useful to prevent industrial spoilage, in particular that caused by bacteria and fungi. Industrial biocides find application in the preservation of paints, latices, adhesives, leather, wood, metal working fluids and cooling water.

One class of compound which can be used as an industrial biocide is based on the isothtazolinone structure. There are many disclosures of isothiazolinone derivatives which are stated to have useful biocidal properties. U.S. Pat. No. 3,761,488 discloses isothiazolinone derivatives in which alkyl, alkenyl, alkynyl, cycloalkyl, aralkyl or aryl groups, which may optionally be substituted, are attached to the nitrogen atom and the 4 and 5 positions are unsubstituted or are substituted with halogen or lower alkyl groups. U.S. Pat. No. 4,165,318 discloses a solution of an isothiazolin-3-one in a polar organic solvent, wherein the solution also contains a stabilising amount of formaldehyde. British Patent Specification 2087388 discloses 4,5-polymethylene-4-isothiazolin-3-ones in which the polymethylene chain has three or four carbon atoms.

A further class of compounds which have found a use as industrial biocides are the 2-halo-2-halomethyl glutaronitriles. Such compounds have been disclosed and claimed in U.S. Pat. No. 3,833,731 inter alia.

Compounds and compositions of the foregoing types, and related compounds of the same general type, are effective to a varying degree, depending on the particular compound or composition, against a range of bacteria and/or fungi. However, to reduce the cost of using these compounds it is desirable to improve their effectiveness as antimicrobial materials.

Compositions have been proposed which contain more than one compound which has antimicrobial properties. In general such compositions show an aggregate of the properties of the compounds present in the composition. Typically such compositions contain one compound which exhibits useful antibacterial properties together with a different compound which exhibits useful antifungal properties.

We have now found that certain compositions possess surprisingly useful antimicrobial especially anti-bacterial properties.

Thus, according to the present invention there is provided a composition which comprises (a) at least one 4,5-polymethylene-4-isothiazolin-3-one or a derivative thereof, and (b) at least one 2-halo-2-halomethyl glutaronitrile The 4,5 polymethylene-4-isothiazolin-3-one derivative which is component a) of the composition is typically a compound of the general formula I.

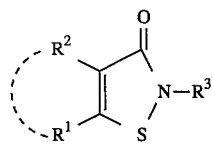

I wherein:

$R^1$ and $R^2$ taken together represent a polymethylene chain, having 3 or 4 carbon atoms or a polymethylene chain having 3 or 4 carbon atoms substituted by at least one lower alkyl radical having from 1 to 4 carbon atoms;

$R^3$ represents hydrogen; a linear or branched alkyl group having from 1 to 12 carbon atoms; a linear or branched alkyl group having from 1 to 3 carbon atoms substituted by one or more hydroxyl groups; an alkenyl group having from 3 to 6 carbon atoms; a radical of the formula

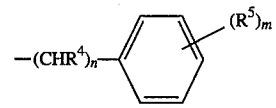

wherein:

n is 0 or 1;

m is 1 or 2;

$R^4$ represents hydrogen or a lower alkyl group; and $R^5$ represents hydrogen, lower alkyl, nitro, trifluoromethyl or halogen, preferably chlorine, bromine or iodine; cyclo alkyl having from 3 to 6 carbon atoms; and a radical of formula

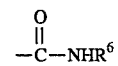

wherein $R^6$ represents hydrogen, linear or branched alkyl having from 1 to 12 carbon atoms or a radical of the formula

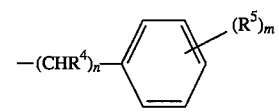

as defined above, and their salts or complex with a mineral or organic acid, or with a base.

In a preferred embodiment of the invention the 4,5-polymethylene-4-isothiazolin-3-one can be represented by the general formula II

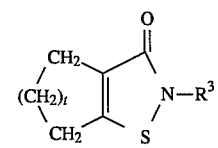

II wherein t is 1 or 2 and $R^3$ is as defined above. These compounds are, thus, derivatives of 4,5-trimethylene or 4,5-tetramethylene-4-isothiazolin-3-ones.

$R^3$, in formulae I and II, may be a linear or branched alkyl group, such as methyl, ethyl, propyl, isopropyl, butyl, isobutyl, tert-butyl, hexyl, octyl or dodecyl.

When $R^3$ represents alkyl substituted by one or more hydroxyl groups, this includes, for instance, hydroxymethyl, 2-hydroxyethyl, 2-hydroxypropyl and 1,2 dihydroxy propyl.

As an example of alkenyl as represented by $R^3$, there may be mentioned allyl.

When R³ represents a radical of formula

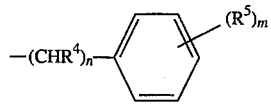

this can be, for example, phenyl, chlorophenyl, 2,4-dichlorophenyl, benzyl, 4-chlorobenzyl or 2,4-dichlorobenzyl.

When R³ represents cycloalkyl having from 3 to 6 carbon atoms, this can be, for example, cyclopropyl, cyclobutyl, cyclopentyl or cyclohexyl.

When R³ represents a radical of formula

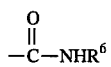

it can be carbomoyl, N-methyl carbamoyl, N-ethylcarbamoyl, N-isopropyl carbamoyl, N-propyl carbamoyl, N-phenyl carbamoyl, N-cyclohexyl carbamoyl, N-butyl carbamoyl or N-octyl carbamoyl.

Finally, when the compound of formula I forms a complex with a base, R³ is a cation. This cation my have a valency of more than one, but is particularly a monovalent cation such as an alkali metal, an amine or quaternary ammonium cation.

The salts formed between the compound of formula I and a mineral or organic acid, and the complexes formed between the compound of formula I and a base are generally water soluble and hence can be used in aqueous solution.

The term lower alkyl represented by R⁴ above includes linear or branched alkyl chains containing up to 4 carbon atoms such as methyl, ethyl, isopropyl, butyl and tertiary butyl.

As specific examples of compounds which may be used as component (a) of the composition of the present invention, there may be mentioned 2-methyl-4,5-trimethylene isothiazolin-3-one (formula II, in which t is 1 and R³ is methyl), and 4,5-trimethylene isothiazolin-3-one (formula II, in which t is 1 and R³ is hydrogen).

Component (b) of the composition of the present invention is at least one compound of general formula

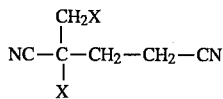

wherein
each X, which may be the same or different, is a halogen atom, especially chlorine or bromine.

Preferably, both substituents X are the same halogen, and are especially bromine atoms.

By way of examples, there may be mentioned 2-chloro-2-chloromethyl glutaronitrile and particularly 2-bromo-2-bromomethyl glutaronitrile.

As a particular embodiment of the present invention there is provided a composition comprising 2-methyl-4,5-trimethylene-4-isothiazoline-3-one and 2-bromo-2-bromomethyl glutaronitrile.

In various types of applications, it is frequently necessary or convenient to formulate the 4,5-polymethylene-4-isothiazolin-3-one in solution, especially using water or polar organic solvents such as alcohols.

When the 4,5-polymethylene-4-isothiazolin-3-ones are used in aqueous solution, their solubility may be improved by forming their salts with strong organic and/or inorganic acids such as hydrochloric, sulphuric, succinic and citric acids.

The relative proportions of the components of the composition can vary, and the composition typically contains one part by weight of component (a) and at least one part by weight of component (b). In general the composition contains one part of component (a) and at least 20 parts by weight of component (b), and in particular the composition contains one part of component (a) and at least 100 parts by weight of component (b).

Compositions having useful properties can be obtained which contain one part by weight of component (a) and up to 2000 parts by weight of component (b). The preferred proportions are dependent on the compounds used as component (a) and component (b), and also the particular system in which the mixture is to be used. In general the composition contains 1 part by weight of component (a) and not more than 800 parts by weight of component (b). Particularity useful effects have been obtained with compositions containing one part of component (a) and not more than 600 parts by weight of component (b).

The compositions of the present invention have antimicrobial properties. We have found that compositions in accordance with the present invention are active against both bacteria and fungi. Furthermore, compositions in accordance with the present invention are such that the sum of the fractional inhibitory concentration (FIC) for all the components of the composition is less than one and, with preferred compositions is less than 0.9. Especially preferred compositions are those in which the sum of the FIC for all the components of the composition is not more than 0.7. The FIC is the ratio of the concentration of an individual component to the minimum inhibitory concentration of that component. It will be appreciated that if the value of the sum of the FIC for all the components of the composition is less than one, the composition is synergistic, the extent of synergy being indicated by theta mount by which the sum of the FIC is below one. We have found that some compositions in accordance with the present invention are such that the sum of the FIC is less than 0.7.

The compositions of the present invention have antimicrobial properties and are suitable for use as industrial biocides. They exhibit good wet state preservation and hence may be used as a cutting fluid preservative and also in cooling water applications. They may also be used in paper mill liquors. Furthermore, the composition may be used to preserve industrially important formulations, especially aqueous based formulations, which are used for coloration, such as dyestuffs and printing inks. They may also be used in the agrochemical industries to preserve formulations such as herbicide and pesticide flowables.

Still further important applications of the compositions of the present invention include their use in hydrocarbon fluids such as diesel fuels. They may also be incorporated into adhesives in order to inhibit microbial spoilage.

The preservation of wood and leather is yet another important application of the compositions.

Especially important is the use of the composition of the present invention in paints, particularly in aqueous based latices.

A particularly preferred use of the compositions of the present invention is the preservation of polyvinyl acrylate and particularly acrylic latices, especially those whose pH is above 7, and especially those containing ammonia or amines.

The materials which are component (a) and component (b) of the composition of the present invention are soluble in many polar solvents, although the solubility is dependent on the nature of the particular compounds which are present in the composition. However, many of the compounds are soluble in water, alcohols, ethers, ketones and other polar solvents or mixtures thereof.

The compositions of the present invention may be used alone as an antimicrobial material but may also be used in, or on, a suitable carrier material.

Thus, as a further aspect of the present invention there is provided a biocide composition comprising a carrier and an effective amount of a composition of components (a) and (b) in accordance with the invention.

The carrier is typically a material which shows little, if any, antimicrobial activity and may be, or include, a material which is susceptible to the growth of micro-organisms, particularly bacteria. The carrier is preferably a liquid medium and the biocide composition may be a solution, suspension or emulsion of the composition of components (a) and (b) in a liquid carrier. The carrier may be water, in which one or both of components (a) and (b) are soluble, or maybe a liquid such as acetic acid, N,N-dimethyl-formamide, propylene glycol, dimethyl sulphoxide or N-methyl-2-pyrrolidone in which at least one, and preferably both, of components (a) and (b) are soluble. Alternatively, a mixture of liquids may be used, one being a solvent for component (a) and component (b) and the other being a non-solvent for both components, and using such a mixture the composition typically comprises an emulsion or droplets of a solution of components (a) and (b) in the solvent therefor dispersed in the non-solvent. If a suspension or emulsion is used, this conveniently contains a surface active agent which is effective to maintain the non-continuous phase as a suspension or emulsion. Any surface active agent known for use in biocide compositions may be used in such a system, for example alkylene oxide adducts of fatty alcohols, alkyl phenols and amines such as ethylene diamine.

Whereas it is advantageous in using the composition of the present invention to add component (a) and component (b) simultaneously, it will be appreciated that in certain circumstances it may be beneficial to add component (a) and component (b) sequentially.

The amount of the composition which is present in the biocide composition may be just sufficient to have an antimicrobial effect or the composition may be present in a substantially greater proportion. It will be appreciated that the biocide composition may be provided as a concentrated solution which is subsequently diluted for use as an antimicrobial material. The higher concentrations of the biocide composition are useful, for example, in the bulk transportation of the composition. Thus, the amount of the composition of components (a) and (b) which is present in the biocide composition is typically in the range from 0.0001% up to 30% by weight of the biocide composition.

The composition of the present invention is especially effective in providing anti-bacterial activity. Thus, the compositions can be used for the treatment of various media to inhibit the growth of micro-organisms.

As a further aspect of the present invention there is provided a method for inhibiting the growth of micro-organisms on, or in, a medium which comprises treating the medium with a composition of components (a) and (b) as hereinbefore defined.

The composition can be used in conditions in which micro-organisms grow and cause problems. Systems in which micro-organisms cause problems include liquid, particularly aqueous, systems such as cooling water liquors, paper mill liquors, metal working fluids, geological drilling lubricants, polymer emulsions and surface coating compositions such as paints, varnishes and lacquers and also solid materials such as wood and leather. The composition of the present invention can be included in such materials to provide an anti-microbial effect. The amount of the composition is typically in the range from 0.0001 up to 10%, preferably 0.001 up to 5% and especially 0.002 to 1% by weight of the composition relative to the system to which it is added. In many cases, microbial inhibition has been obtained with between 0.005% and 0.1% by weight of the composition.

Components (a) and (b) of the composition of the present invention may be the only antimicrobial compounds or may be used together with further compounds having antimicrobial characteristics. The composition may contain more than one compound which is component (a) together with one or more compounds which is component (b). Alternatively, a composition of components (a) and (b) in accordance with the present invention may be used together with one or more known antimicrobial compounds. The use of a mixture of anti-microbial compounds can provide a composition having a broader anti-microbial spectrum and hence one which is more generally effective than the components thereof. The known antimicrobial may be one possessing anti-bacterial, anti-fungal, anti-algal or other antimicrobial characteristic. The mixture of the composition of the present invention with other antimicrobial compounds typically contains from 1 to 99% by weight, relative to the weight of total antimicrobially active compounds, of the composition of components (a) and (b), and particularly from 40 to 60% by weight of the composition of components (a) and (b).

As examples of known antimicrobial compounds which may be used, together with the composition of the present invention, there may be mentioned quaternary ammonium compounds such as diethyldodecylbenzyl ammonium chloride; dimethyloctadecyl(dimethylbenzyl)ammonium chloride; dimethyldidecylammonium chloride; dimethyldidodecylammonium chloride; trimethy-tetradecylammonium chloride; benzyldimethyl($C_{12}$–$C_{18}$ alkyl)ammonium chloride; dichlorobenzyldimethyldodecylammonium chloride; hexadecylpyridinium chloride; hexadecylpyridinium bromide; hexadecyltrimethylammonium bromide; dodecylpyridinium chloride; dodecylpyridinium bisulphate; benzyldodecyl-bis(beta-hydroxyethyl)ammonium chloride; dodecylbenzyltrimethylammonium chloride; benzyldimethyl($C_{12}$–$C_{18}$ alkyl)ammonium chloride; dodecyldimethylethyl ammonium ethylsulphate; dodecyldimethyl-(1-naphthylmethyl)ammonium chloride; hexadecyldimethylbenzyl ammonium chloride; dodecyldimethylbenzyl ammonium chloride and 1-(3-chloroallyl)-3,5,7-triaza-1-azonia-adamantane chloride; urea derivatives such as 1,3-bis(hydroxymethyl)-5,5-dimethylhydantoin; bis(hydroxymethyl)urea; tetrakis(hydroxymethyl)acetylene diurea; 1-(hydroxymethyl)-5,5-dimethylhydantoin and imidazolidinyl urea; amino compounds such as 1,3-bis(2-ethylhexyl)-5-methyl-5-aminohexahydropyrimidine; hexamethylene tetra amine; 1,3-bis(4-aminophenoxy)propane; and 2-[(hydroxymethyl)amino]ethanol; imidazole derivatives such as 1[2-(2,4-dichlorophenyl)-2-(2-propenyloxy)ethyl]-1H-imidazole; 2-(methoxycarbonylamino)-benzimidazole; nitrile compounds such as 2,4,5,6-tetrachloroisophthalodinitrile; thiocyanate derivatives such as methylene bis thiocyanate; tin compounds or complexes such as tributyltin-oxide, chloride, naphthoate, benzoate or 2-hydroxybenzoate; thiazole derivatives such as 2-(thiocyanomethylthio)-benzthiazole; and mercaptobenzthiazole; nitro compounds such as tris(hydroxymethyl)nitromethane; 5-bromo-5-nitro-1,3-dioxane and 2-bromo-2-nitropropane-1,3-diol; aldehydes and derivatives such as gluteraldehyde (pentanedial) p-chlorophenyl-3-iodopropargyl formaldehyde and glyoxal; amides such as chloracetamide; N,N-bis(hydroxymethyl)chloracetamide; N-hydroxymethyl-chloracetamide and dithio-2,2-bis(benzmethyl amide); guanidine derivatives such as poly hexamethylene biguanide and 1,6-hexamethylene-bis[5-(4-chlorophenyl)biguanide]; thiones such as 3,5-dimethyltetrahydro-1,3,5-2H-thiodiazine-2-thione; triazine derivatives such as hexahydrotriazine and 1,3,5-tri-(hydroxyethyl)-1,3,5-hexahydrotriazine; oxazolidine and derivatives thereof such as bis-oxazolidine; furan and derivatives thereof such as 2,5-dihydro-2,5-dialkoxy-2,5-dialkylfuran; carboxylic acids and the salts and esters thereof such as sorbic acid and the salts thereof and 4-hydroxybenzoic acid and the salts and esters thereof; phenol and derivatives thereof such as 5-chloro-2-(2,4-dichlorophenoxy)phenol; thio-bis(4-chlorophenol) and 2-phenylphenol; sulphone derivatives such as diiodomethyl-paratolyl sulphone, 2,3,5,6-tetrachloro-4-(methylsulphonyl)pyridine and hexachlorodimethyl sulphone.

Further aspects of the present invention are described in the following illustrative examples.

In the following examples, compositions in accordance with the present invention were subjected to evaluation of the antimicrobial properties of the compositions. The evaluation was effected, under sterile conditions throughout, as follows:

In the microbiological evaluation, various compositions were tested for anti-microbial activity against bacteria and fungi. The bacterium used was *Escherichia coli* and the fungus used was *Aspergillus niger*.

Microbiological evaluation

The materials, or mixture of materials, to be tested were added to a nutrient broth in amounts to give a desired concentration of the added material. The added materials were added at concentrations from zero to above the minimum inhibitory concentration of the particular material. In the mixtures, the concentrations of each material were varied in a systematic fashion to give a matrix of mixtures of different relative proportions and different total concentrations.

The effect on the inhibition of growth of bacteria was investigated by inoculating each sample of broth with sufficient of the test bacterium to give about $10^5$ cells cm$^{-3}$. The mixture was incubated at 30° C. for 48 hours. At the end of the test period the presence of turbidity in the broth indicated that growth of the test bacterium had occurred. A lack of turbidity was indicative that no growth had occurred. The results were used to draw an isobologram from which the sum of the fractional inhibitory concentration for a mixture can be determined.

EXAMPLE 1

The microbiological evaluation as described was carried out using the bacterium, *Escherichia coli*. The composition tested was a mixture of 2-methyl-4,5-trimethylene-4-iisothiazolin-3-one and 2-bromo-2-bromomethyl glutaronitrile.

An isobologram was drawn utilising concentrations of 0, 110, 221, 332, 444, 555, 665, 777, 888 and 1000 microgram cm$^{-3}$ of the glutaronitrile and 0, 0.2, 0.5, 0.7, 0.9, 1.1, 1.4, 1.6, 1.8 and 2 microgram cm$^{-3}$ of the isothiazolinone.

From the results obtained, it was found that the lowest sum of the fractional inhibitory concentration (FIC) was 0.61 which was achieved with a mixture containing 110 microgram cm$^{-3}$ of the 2-bromo-2-bromomethyl glutaronitrile and 0.2 microgram cm$^{-3}$ of the 2-methyl-4,5-trimethylene-4-isothiazolin-3-one. This may be contrasted with the minimum inhibitory concentrations (MIC) of the two individual components against the same micro-organism, which were found to be 221 microgram cm$^{-3}$ and 1.8 microgram cm$^{-3}$, respectively.

EXAMPLE 2

Example 1 was repeated, except the bacterium used was replaced by the fungus, *Aspergillus niger*.

Again, an isobologram was drawn utilising concentrations of 0, 166, 333, 500, 666, 833, 1000, 1166, 1333 and 1500 microgram cm$^{-3}$ of the glutaronitrile and 0, 55, 111, 166, 221, 277, 332, 388, 444 and 500 microgram cm$^{-3}$ of the isothiazolinone.

From the results obtained, it was found that the lowest sum of the FIC was 0.67 which was achieved! with a mixture containing 500 microgram cm$^{-3}$ of the 2-bromo-2-bromomethyl glutaronitrile and 111 microgram cm$^{-3}$ of the 2-methyl-4,5-trimethylene-4-isothiazolin-3-one. Again, this may be contrasted with the two MIC values against the same micro-organism which were found to be 1500 and 332 microgram cm$^{-3}$, respectively.

I claim:

1. A medium which is susceptible to attack by micro-organisms and which contains from 0.0001 to 10% by weight of the medium of a composition having a fractional inhibitory concentration of less than one which comprises an effective amount of (a) 2-methyl-4,5-trimethylene-4-isothiazolin-3-one, and (b) 2-bromo-2-bromomethyl glutaronitrile.

2. A medium as claimed in claim 1 which contains one part by weight of component (a) for up to 2000 parts by weight of component (b).

3. A medium as claimed in claim 2 which contains one part by weight of component (a), for not more than 800 parts by weight of component (b).

4. A medium as claimed in claim 3 which contains one part by weight of component (a) for not more than 600 parts by weight of component (b).

5. A medium as claimed in claim 4 wherein the sum of the fractional inhibitory concentration of the components is less than 0.7.

6. A medium as claimed in claim 5 which additionally includes a carrier.

7. A medium as claimed in claim 1 which contains from 0.005 to 1% by weight of the medium of said composition.

8. A medium as claimed in either claim 1 or claim 7 which contains from 0.005 to 0.1% by weight of the medium of said composition.

9. A medium as claimed in either claim 1 or claim 7 which is selected from a cooling water system, a paper mill liquor, a metal working fluid, a geological drilling lubricant, a polymer emulsion, a paint, a lacquer, a varnish, a hydrocarbon fluid, an adhesive, a dyestuff or ink formulation, an agrochemical formulation, leather or wood.

10. A paint medium as claimed in claim 9 which is an acrylic latex.

11. A medium as claimed in claim 8 which is selected from a cooling water system, a paper mill liquor, a metal working fluid, a geological drilling lubricant, a polymer emulsion, a paint, a lacquer, a varnish, a hydrocarbon fluid, an adhesive, a dyestuff or ink formulation, an agrochemical formulation, leather or wood.

12. A paint medium as claimed in claim 11, which is an acrylic latex.

13. A medium according to claim 1, said medium being a cooling water system containing from 0.0001 to 10% by weight of 2-methyl-4,5-trimethylene-4-isothiazolin-3-one and 2-bromo-2-bromomethyl glutaronitrile.

* * * * *